United States Patent [19]

Vellekoop et al.

[11] Patent Number: 4,765,984

[45] Date of Patent: Aug. 23, 1988

[54] STABLE SINGLE UNIT DOSE ORAL PRODUCT

[75] Inventors: Linda J. Vellekoop, Neshanic; Jordan Barth, East Brunswick, both of N.J.

[73] Assignee: Colgate-Palmolive Company, New York, N.Y.

[21] Appl. No.: 939,892

[22] Filed: Dec. 16, 1986

Related U.S. Application Data

[63] Continuation-in-part of Ser. No. 821,567, Jan. 22, 1986, Pat. No. 4,705,680.

[51] Int. Cl.⁴ .................................................. A61K 9/68
[52] U.S. Cl. ..................................... 424/441; 424/464; 424/48; 424/49; 424/57; 424/58
[58] Field of Search ............................... 424/49, 57–58, 424/441, 464, 48

[56] References Cited

U.S. PATENT DOCUMENTS

| | | | |
|---|---|---|---|
| 4,112,066 | 9/1978 | Hussein | 424/48 |
| 4,303,648 | 12/1981 | Witzel et al. | 424/49 |
| 4,353,890 | 10/1982 | Scott | 424/58 |
| 4,414,198 | 11/1983 | Michaelson | 424/441 |
| 4,525,342 | 6/1985 | Weiss et al. | 424/49 |
| 4,533,543 | 8/1985 | Morris et al. | 424/441 |

OTHER PUBLICATIONS

Kelco, Structured Foods with the Algin/Calcium Reaction, Technical Bulletin F-83, Jan. 1984.

Primary Examiner—J. R. Brown
Assistant Examiner—F. T. Moezie
Attorney, Agent, or Firm—Robert L. Stone; Murray M. Grill

[57] ABSTRACT

A single unit dose chewable oral product stabilized against syneresis comprising an alginate gelling agent, cross-linked with a calcium ion, flavor and a liquid vehicle containing water, humectant and a vegetable oil additive to reduce syneresis.

11 Claims, No Drawings

STABLE SINGLE UNIT DOSE ORAL PRODUCT

This application is a continuation-in-part of U.S. patent application Ser. No. 821,567, filed Jan. 22, 1986, now U.S. Pat. No. 4,705,680.

FIELD OF THE INVENTION

This invention relates to stable single unit dose, discrete, non-sagging forms of dentifrice, mouthrinse or other oral products comprising an alginate crosslinked with a calcium ion, a flavor and a liquid vehicle containing water, humectant and a vegetable oil additive; and the method of preparing said unit dose oral product which comprises shaping, by extrusion or molding, an alginate gel mixture comprising sodium alginate, flavor, humectant, water, vegetable oil and other conventional dental ingredients into discrete unit dose forms, immersing said shaped unit dose form into an aqueous setting bath containing a calcium ion to gel or solidify said shaped unit forms rinsing said gelled unit dose forms, drying said unit dose forms and packaging said unit dose forms. A single unit dose mouthwash can also be made by surrounding the active mouthwash with a shell of sodium alginate, extruding said encapsulated mouthwash into shaped units which are immersed into a calcium ion-containing setting bath wherein a calcium alginate shell is formed around the mouthwash.

BACKGROUND AND PRIOR ART

Parent U.S. patent application Ser. No. 821,567, filed Jan. 22, 1986, now U.S. Pat. No. 4,705,680 discloses dental creams stabilized against syneresis by the addition of a vegetable oil to the liquid vehicle.

Syneresis (liquid exudation from a paste product) is a serious consumer observable problem which will mar the cosmetic properties of a dentifrice. This effect is a serious problem in a paste product and is an even more serious problem in a self standing unit dose form.

Single unit dose forms of dentifrice, mouthrinse or other oral products have been considered desirable for many years. However, previous products such as a crushable tablet and a chewable but non crushable tablet did not appear to be acceptable to the consumer either practically or aesthetically.

The prior art discloses chewable shaped and molded unitary products for cleaning teeth and as a mouth freshener comprising gelatin, water, glycerin and a vegetable gum such as gum acacia as the gelling agent or binder for the other ingredients in U.S. Pat. No. 3,422,184. Other optional ingredients are included such as dental polishing agents, sweetening agents, antibacterial agents, flavoring agents, coloring agents and preservatives. No vegetable oil and no alginate crosslinked with a calcium ion is disclosed herein.

U.S. Pat. No. 4,060,602 discloses oral preparations for preventing dental caries containing about 0.03–1% by weight of pimento berry oil or terpeneless bay oil as the antimicrobial agent in dental compositions including lozenges or troches by mixing with mucilage or gelatin and water. Chewing gums containing a standard gum base may also be prepared with the antibacterial bay oil component. No crosslinked calcium alginate is disclosed herein, nor does the composition contain vegetable oil to control syneresis.

U.S. Pat. No. 4,525,342 also discloses a mouthwash or toothpaste containing vegetable oil to desorb microorganisms, in large amounts of 33–97% by weight of the oil phase. This product is delivered from a double squirt bottle, one compartment containing the oil phase and the other compartment containing an aqueous phase comprising water soluble conventional dental components such as alginate, saccharin, sodium monofluorophosphate, etc. This is totally different from present novel chewable single unit dose form containing an alginate crosslinked with calcium.

U.S. Pat. No. 4,157,386 discloses a soft chewable lozenge comprising a dry mixture of polishing agent, a fluoride ion source, a starch adhesive, an unsaturated vegetable oil as a viscosity builder and softening agent, and a non-cariogenic sweetener such as xylitol or sorbitol. No alginate crosslinked with a calcium ion is disclosed herein.

The use of sodium alginate both as a thickening agent in a gum base and as a hydrocolloidal coating for water-insoluble therapeutic agents is disclosed in U.S. Pat. No. 4,238,475, wherein is described a chewing gum capable of releasing therapeutic water-insoluble materials. The chewing gum comprises therapeutic particles precoated with a hydrocolloid such as gum arabic, dextrin, gum tragacinth, gelatin, pectin, carboxymethyl cellulose or alginate in a gum base containing two sweeteners, a plasticizer or aqueous softener in the form of a polyhydric alcohol-type syrup, and a thickener such as alginate, carrageenan, xanthan gums and other water-soluble gums, and a flavor derived from plants, leaves, etc. such as citris oils, peppermint oil, clove oil, bay oil and the like. There is no disclosure therein of alginate crosslinked with a calcium ion, which is the basis of present novel chewable tablet or lozenge.

U.S. Pat. No. 4,532,126 discloses a chewable filled soft elastic gelatin capsule, which includes a shell formed from a molten gel mass containing gelatin, water, plasticizer such as glycerin or sorbitol and an insoluble masticatory substance such as natural gums, rubber, paraffin, petroleum, wax, etc; and a filling material such as candy, breath fresheners, cough preparations and the like. The filling is incapsulated in the gel mass on conventional rotary die-encapsulation equipment. There is no disclosure of an alginate crosslinked with a calcium ion in the encapsulating gel mass.

European Pat. No. 0,181,179 discloses antimicrobial lozenge containing a cationic therapeutic agent and a solid nonionic lubricant such as hydrogenated vegetable oil prepared by mixing the flavor, therapeutic agent, filler (sorbitol) and lubricant and transferring the powder mixture to a tablet press to form tablets. No gelling agent is used in this composition, and the solid vegetable oil tableting lubricant constitutes 1% by weight of the composition.

Kelco Brochure, *Structural Foods With the Algin/Calcium Reaction*, Technical Bulletin F-83, January 1984, describes the formation of structured (gelled) foods with alginates via the algin/calcium reaction, using three major gelling methods. The diffusion setting method consists in allowing the calcium ions to diffuse slowly into an alginate solution using a two-mix system, i.e. a fruit/sugar mix is encapsulated with a thin coat of sodium alginate/sugar/water solution prior to immersing in an aqueous calcium/malic acid/sugar setting bath. The internal or bulk setting method consists in rapid mixing two mixes, one containing the alginate and the calcium ion source, dicalcium phosphate; and the other mix contains fruit puree, sequestrant and acid; and allowing the final mixture to set under shear-free conditions. The setting by cooling method consists in dissolving the alginate, calcium salt, acid and sequestrant in hot water and allowing the solution to set by cooling.

However, there is no disclosure of the use of the alginate/calcium gellation reaction in the formation of single unit dose dental products comprising an alginate crosslinked with a calcium ion, a flavor, vegetable oil, humectant and water. In addition, none of the three described processes of making structured (gelled) foods disclose present novel method of first forming shaped single dose discrete unit forms of the sodium alginate mixture which may contain all the dental components, or may be a shell surrounding a unit dose of active mouthwash; and then immersing said shaped unit forms into a setting bath containing a calcium ion source, rinsing said gelled unit forms, drying and packaging said unit dose forms.

SUMMARY OF THE INVENTION

The primary object of this invention is to provide a stable single unit dose oral product in free standing form, stabilized against syneresis.

Another object of this invention is to provide a stable single unit dose form of a dentifrice or mouthwash or mouth freshener or other oral product.

Another object of instant invention is to provide a mechanism that renders the product acceptable and practical to the consumer, in the form of a chewable unit dose oral product.

Still another object of present invention is to provide a mechanism for the preparation of unit dose forms for dental use comprising an alginate crosslinked with a calcium ion, flavor, a liquid vehicle, containing water, humectant, and a vegetable oil in an amount effective to improve the liquid holding properties of the unit dose dental product and control syneresis.

Another object of present invention is to provide a convenient unit dose product such as a chewable bead or lozenge which changes in form on usage from a solid to a pasty consistency.

To achieve the foregoing and other objects in accordance with the present invention, as embodied and broadly described herein, the stable chewable single unit dose oral product of the invention comprises about 0.4-1.5% by weight of sodium alginate crosslinked with a calcium ion, flavor, about 2-15% by weight of a vegetable oil, humectant and water. The dental or oral product may be a single unit dose form of a dentifrice or a mouthrinse or mouth freshener.

More specifically, present invention relates to a method of preparing a stable single unit dose oral product which comprises shaping an alginate gel mixture comprising sodium alginate flavor, humectant, water and a vegetable oil, into discrete single unit dose form; immersing said shaped unit dose form into an aqueous setting bath containing a calcium ion which crosslinks with the sodium alginate and gels said discrete single unit dose form; rinsing said gelled unit in deionized water; drying said unit dose form and packaging said single dose units.

A novel discrete unit dose form has now been found, which is both practical and acceptable to the consumer. The mechanism for the preparation of this unit dose form is based on the alginate crosslinked with calcium ion reaction. The entire mass of the single unit dose can be an alginate crosslinked with a calcium ion; or a mouthwash can be placed in the center of the product and surrounded by the calcium alginate shell. The solid unit dose form has the advantage of controlling the amount of product used in a single application. They are also more portable and do not require that one carry around a tube full of product. The unit dose product conveniently provides a single application with ease, which can be used anywhere, and is particularly useful between brushings. Another advantage and unique property of present unit dose product is that upon chewing, the product changes from a solid to a pasty or dentifrice type consistency.

The unit dose oral product in accordance with present invention may be a unit dose form of dentifrice, or a unit dose form of mouthrinse or a unit dose form of other oral products. The shape of the unit dose form which is chewable may be round, oval, square or rectangular. The composition is completely edible and leaves no solid residue.

The unit dose forms may optionally be coated with a coating material such as waxes, shellac, carboxymethyl cellulose, polyethylene/malic anhydride copolymer or kappa-carrageenan to increase its water impermeability and its chewing time. Both the uncoated and coated unit dose form have particular utility for cleansing the teeth and freshening the mouth after meals in situations where tooth brushing is impossible. It has been found that chewing the unit dose forms of present invention results in extensive removal of trapped food particles and greatly reduces the level of fermentable carbohydrate material which contributes to caries formation in the mouth. The mouth is cleaned and freshened easily and provides a sustained release rate of active ingredients typically for at least 2 minutes or longer. Accordingly, the solid dose oral compositions of this invention afford a longer time period of contact with the active ingredients in the mouth than a toothpaste, toothpowder or mouthrinse which is in contact with the mouth only about 30-90 seconds of brushing or rinsing.

In accordance with the present invention, the alginates (monovalent salt) crosslinked with calcium ion is the essential component in, and mechanism for the preparation of unit dose forms of dentifrice, mouthwash and other oral products. Although the alginate-calcium reaction is well known, it has not been used in the formation of discrete unit dose forms of dental products. The monovalent alginates such as sodium alginate are hydrophilic colloids derived from a variety of weed sources. The alginates have many uses such as a protective colloid, for thickening solutions, for forming films on drying, for textile dressing and for synthetic fibers. Alginate is a linear copolymer composed of two monomeric units, D-mannuronic acid and L-guluronic acid. When calcium ions are added to sodium alginate, they replace the sodium ions and the alginate crosslinks with the calcium ion, the gelation or solidification occurs. The source of the calcium ion is a water soluble or partially water-soluble calcium salt having at least 5% solubility in water (such as calcium chloride, calcium lactate, calcium sulfate, calcium carbonate, dicalcium phosphate and the like, in an aqueous setting bath. The amount of sodium alginate in present unit dose formulation is about 0.4 to 1.5% and preferably about 0.5 to 1.0% by weight. The setting bath should have a sufficient concentration of the calcium salt to provide calcium ions for crosslinking with the alginate to effect gelation of the formulation. An aqueous solution containing about 5-10% by weight of the calcium salt is satisfactory.

The liquid vehicle in the single unit dose products of present invention comprises water, glycerin and/or sorbitol humectant, and a vegetable oil additive to reduce syneresis.

The vegetable oil is an essential component of the formulation in accordance with this invention. Vegetable oils are liquids and disperse readily in the liquid vehicle, and while providing desirable sensory effect are also effective to prevent the solid unit dose oral products from undergoing syneresis. In the absence of the vegetable oil component in the formulation, syneresis occurs at room temperature. Vegetable oils are obtained by extraction of oil from seeds of plants, particularly vegetable or fruit plants. They are well described in *Vegetable Fats and Oils*, Jamieson, Chemical Catalog Company, Inc., New York, 1932 and *Food Industries Manual*, 20th Edition, Woollen, Chemical Publishing Co., New York, 1970. Many particular vegetable oils are listed in appendix Tables 12, 16, 17 and 18 of *Vegetable Fats and Oils* (pages 414–423) and in Table 6.1 of Food Industries Manual, 20th Edition (pages 200–201). Of the vegetable oils, coconut oil, palm oil, avocado oil, peanut oil and safflower oil are observed as particularly effective in reducing syneresis. Vegetable oil is employed in the unit dose forms in an amount of about 2–15% by weight, preferably about 5–10% by weight.

The liquid vehicle in the formulation of the single unit dose form of a dentifrice comprises water, glycerin and sorbitol in an amount of at least about 40% by weight, and will generally be about 40–75% by weight of the formulation. The water content is about 10–50% and preferably about 15–35% by weight. The glycerin and sorbitol together generally comprise about 20–50%, and preferably about 20–45% by weight of the formulation.

The liquid vehicle in the formulation of the single unit dose form of a mouthwash constitutes about 55–95% by weight liquid comprising about 50–80% water and about 5–15% glycerin or sorbitol or a combination of both humectants.

Any suitable flavoring or sweetening materials may be employed in formulating a flavor for the composition of the unit dose forms of present invention. Examples of suitable flavoring constituents include the essential flavoring oils, e.g., oils of spearmint, peppermint, wintergreen, sassafras, clove, sage, eucalyptus, majoram, cinnamon, lemon and orange, as well as methyl salicylate. Essential oils are typically extracted from rind. They are not seed extracts as are vegetable oils. Suitable sweetening agents include sucrose, lactose, maltose, xylitol, sodium 6-methyl-3, 4-dihydro-1,2,3-oxathiazine-4-one, sodium cyclamate, perillartine and sodium saccharin. Oleoresins such as capsicum may also be used. Suitably flavor and sweetening agents may together comprise from about 0.1 to 5% of the compositions of the instant invention.

The unit dose form of dentifrice, in accordance with present invention, preferably contains a dentally acceptable water-insoluble polishing agent in an amount of about 5–25% and preferably about 10–20% by weight. Typical polishing agents include finely divided alkaline earth metal salts such as dicalcium phosphate dihydrate, anhydrous dicalcium phosphate, calcium carbonate, tricalcium phosphate, calcium pyrophosphate, dimagnesium phosphate trihydrate, magnesium carbonate; hydrated alumina and calcined alumina; silica; aluminum silicates, zwirconium silicate, sodium aluminosilicates and mixtures thereof.

Another preferred ingredient in the unit dose form of dentifrice is a substantially water soluble gelling agent or gum such as iota carrageenan, kappa-carrageenan, sodium carboxymethyl cellulose, methyl cellulose, hydroxyethyl cellulose, hydroxypropyl cellulose, xanthan, gum arabic, in amounts of about 0.5–1.5% by weight of the total formulation, and preferably in the weight ratio of about 1:1.6 to 2:1 of sodium alginate:gum. Iota carrageenan is preferred due to its ability to form a complex with calcium.

Any suitable or compatible surface-active or detersive material may be incorporated in the unit dose dental products of present invention. Such compatible materials are desirable to provide additional detersive, foaming and antibacterial properties depending upon the specific type of surface-active material and are selected similarly. These detergents are water-soluble organic compounds usually, and may be anionic, nonionic, or cationic in structure. Suitable detersive materials are known and include, for example, the water-soluble salts of higher fatty acid monoglyceride monosulfate detergent (e.g., sodium coconut fatty acid monoglyceride monosulfate), higher alkyl sulfates (e.g., sodium lauryl sulfate), alkyl aryl sulfonate (e.g. sodium dodecyl benzene sulfonate), methylcocoyl taurate, higher fatty acid esters of 1,2-dihydroxypropanesulfonate) and the like.

Further detersive materials include the substantially saturated higher aliphatic acyl amides of lower aliphatic amino carboxylic acid compounds, such as those having 12 to 16 carbons in the acyl radical. The amino acid portion is derived generally from the lower aliphatic saturated monoamino carboxylic acids having about 2 to 6 carbons, usually the monocarboxylic acid compounds. Suitable compounds are the fatty acid amides of glycine, sarcosine, alanine, 3-aminopropanoic acid and valine having about 12 to 16 carbons in the acyl group. It is preferred to use the N-lauroyl myristoyl and palmitoyl sarcoside compounds, however, for optimum effects.

The amide compounds may be employed in the form of the free acid or preferably as the water-soluble salts thereof, such as the alkali metal, ammonium, amine and alkylolamine salts. Specific examples thereof are sodium and potassium N-lauroyl, myristoyl and palmitoyl sarcosides, ammonium and ethanolamine, N-lauroyl sarcoside, N-lauroyl sarcosine and sodium N-lauroyl glycine and alanine. For convenience herein, reference to "amino carboxylic acid compound", "sarcoside", and the like refers to such compounds having a free carboxylic group or the water-soluble carboxylate salts.

Other suitable surface-active materials include nonionic agents such as condensates of sorbitan monostearate with approximately 20 moles of ethylene oxide, sorbitan diisostearate condensed with 40 moles of polyethylene glycol, condensates of ethylene oxide with propylene glycol ("Pluronic" material), and castor oil ester (e.g. Cremophor EL); and amphoteric agents such as quaternized imidazole derivatives, which are available under the trade mark MIRANOL such as MIRANOL C2M. The preferred nonionic surfactants are the condensates of sorbitan monostearate or diisostearate with 20 to 40 moles of ethylene oxide or polyethylene glycol.

Cationic surface active germicides and anti-bacterial compounds such as diisobutylphenoxyethoxyethyl dimethyl benzyl ammonium chloride, tertiary amines having one fatty alkyl group (of from 12–18 carbon atoms) and two (poly)oxyethylene groups attached to the nitrogen (typically containing a total of from 20 to 50 ethanoxy groups per molecule) and salts thereof with acids, and compounds of the structure:

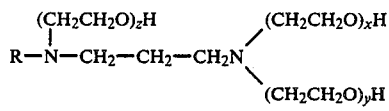

wherein R is a fatty alkyl group typically containing from 12 to 18 carbon atoms, and x, y and z total 3 or higher, as well as salts thereof with mineral or organic acids, may also be used.

The most preferred surfactant is an anionic material, particularly sodium lauryl suflate. The various surface-active materials may be used in any suitable amount, generally from about 0.05 to about 5% by weight, and preferably from about 0.5 to 2% by weight of the unit dose dental products.

The unit dose dental product may also contain a fluorine-containing compound having a beneficial effect on the care and hygiene of the oral cavity, e.g. diminution of enamel solubility in acid and protection of the teeth against decay. Examples thereof include sodium fluoride, stannous fluoride, potassium fluoride, potassium stannous fluoride ($SnF_2.KF$), sodium hexafluorostannate, stannous chlorofluoride, sodium fluorozirconate, and sodium monofluorophosphate. These materials which disassociate or release fluorine-containing ions in water, suitably may be present in an effective but non-toxic amount, usually within the range of about 0.01 to 0.1% by weight of the water soluble fluorine content thereof.

The unit dose dental product of present invention may also contain antiplaque and antitartar agents including physiologically acceptable zinc compounds including the water soluble and sparingly water soluble organic and inorganic zinc salts which provide at least about 0.1 mg of zinc ions per ml of water. The water-soluble zinc salts (at least 1% soluble) are preferred, especially the zinc halides and zinc acetate. Among sparingly soluble zinc salts, zinc citrate is preferred. Examples of suitable zinc salts that may be employed include: zinc stearate; zinc acetate; zinc ammonium sulfate; zinc bromide; zinc chloride; zinc chromate; zinc citrate; zinc dithionate; zinc fluosilicate; zinc tartarate; zinc fluoride; zinc formate; zinc iodide; zinc nitrate; zinc phenol sulfonate; zinc salicylate; zinc sulfate; zinc gluconate; zinc succinate; zinc glycerophosphate. Other zinc salts disclosed in U.S. Pat. No. 4,138,477 having a solubility of at least about 0.01 mg of zinc ions per ml of water are incorporated herein by reference. The zinc compound is present in amounts to provide about 0.05–1% by weight zinc.

Other antiplaque and antitartar agents include the cationic microbial agents such as the quaternary ammonium compounds such as cetyl pyridinium chloride, dodecyl trimethyl ammonium bromide, tetradecyl pyridinium chloride, tetradecyl ethyl pyridinium chloride, dodecyl dimethyl (2-phenoxyethyl) ammonium bromide, benzyl dimethylstearyl ammonium chloride, cetyl pyrridinium chloride, quaternized 5-amino-1,3-bis (2-ethylhexyl)-5-methylhexahydro pyrimidine, benzethonium chloride. Other compounds are the bis [4-(R-amino)-1-pyridinium] alkanes disclosed in U.S. Pat. No. 4,206,215 incorporated herein by reference; and (p-chlorobenzyl dimethyl ammonium) octane dichloride. Other cationic antimicrobial compounds are the substituted guanidines such as chlorhexidine and the compounds such as:
$N^1$-(4-chlorobenzyl)-$N^5$-(2,4 dichlorobenzyl) biguanide
p-chlorophenyl biguandie;
4-chlorobenzhydryl biguanide;
4-chlorobenzhydrylguanylurea;
N-3-lauroxypropyl-N-p-chlorobenzylbiguanide;
1,6-di-p-chlorophenylbiguanide hexane;
1,6-bis-(2-ethyl hexylbiguanide) hexane
5,6-dichloro-2-guanidinobenzimidazole;
$N^1$-p-chlorophenyl-$N^5$-laurylbiguanide
and their non-toxic acid addition salts.

Minor amounts of coloring agents, dyes or ultraviolet absorbers to enhance the color, and the like so as to improve the aesthetic value and consumer acceptability, may also be included in the unit dose forms of present invention. Whitening agents such as titanium dioxide and preservatives such as sodium benzoate may also be added.

The adjuvants are incorporated in the instant composition in amounts which do not substantially adversely affect the properties and characteristics desired and are selected and used in proper amounts depending upon the particular type of composition involved.

The oral preparations should have a pH practicable for use. The pH range of about 5–10, preferably about 6–7, is considered the most practicable for use. Suitable pH adjusting agents include saccharin acid, citric acid, malic acid, adipic acid, succinic acid and the like.

The mechanism for the preparation of unit dose forms of oral formulations, in accordance with present invention, is based on the alginate/calcium reaction, and comprises molding or extruding an alginate gel mixture into a shaped unit dose form, immersing said shaped unit dose forms into a setting bath containing a calcium ion, recovering gelled unit dose forms from the setting bath, rinsing said gelled unit dose forms, drying said rinsed unit dose forms, and packaging said unit dose forms for convenient use. These discrete unit dose forms are non-sagging and may be individually wrapped or multiple units may be packaged on paper strips or in vials of all sizes.

The extrusion technique of extruding droplets of the alginate gel mixture into an aqueous calcium chloride solution is the preferred method of shaping the unit dose forms. The droplets will form beads and float to the surface. The beads are removed from the solution and rinsed in deionized water, and dried at room temperature or in a forced air convection oven.

In the preparation of a unit dose mouthwash, the active mouthwash ingredient may be placed in the center of the alginate mixture and is surrounded by the calcium alginate shell, forming an encapsulated mouthwash.

The alginate gel mixture is prepared by thoroughly mixing the sorbitol and/or glycerine, the flavor, vegetable oil, the sodium alginate, water and other dentifrice ingredients in a suitable blender to form a fluid mixture which is shaped, gelled or solidified, rinsed and dried. The final product is a single dose oral product which is opaque or transparent in appearance and of smooth consistency which changes from a solid to a paste upon chewing.

DETAILED DESCRIPTION OF THE INVENTION

The following specific examples are further illustrative of the present invention, but is is understood that the invention is not limited thereto. All amounts of various ingredients are by weight unless otherwise specified.

EXAMPLE 1

Unit Dose Form of Dentifrice

| Ingredients | % |
|---|---|
| Part I | |
| Glycerine 99.3% | 25.00 |
| Sorbitol 70% Soln | 20.48 |
| Iota Carrageenan | 0.80 |
| Na Alginate | 0.50 |
| Sodium Saccharin | 0.20 |
| Sodium Benzoate | 0.50 |
| Silica containing combined alumina (circa 1%)[1] | 1.00 |
| Deionized Water | 20.00 |
| Sodium Chloride | 1.00 |
| Part II | |
| Huber Zeo 49 | 19.00 |
| Coconut Oil | 10.00 |
| Sodium Lauryl Sulfate | 0.80 |
| Titanium Dioxide | 0.40 |
| Flavor | 0.30 |
| Capsicum | 0.02 |

[1] ZEO 49-JM Huber Co.

A mixture of Part I ingredients is blended with a mixture of Part II ingredients forming a fluid alginate gel mixture which is extruded into an aqueous setting bath containing 6% calcium chloride in the form of droplets. The droplets gel into solid unit dose forms which are removed from the setting bath and rinsed with deionized water and dried. The final product is a white opaque round or oval unit dose chewable dentifrice weighing 1-5 and preferably 3 grams, and exhibits no syneresis.

Chewing the unit dose dentifrice provides extensive removal of trapped food particles and substantial reduction of caries causing fermentable carbohydrate in the mouth. The mouth is cleansed and freshened quickly and easily.

The formulation of a unit dose dentifrice form of the alginate gel mixture of Example 1, in the absence of the coconut oil, resulted in syneresis of the unit dose form at room temperature.

EXAMPLE 2

Example 1 is repeated except that safflower oil is substituted for the coconut oil, yielding a chewable unit dose dentifrice effective similar to Example 1.

EXAMPLE 3

Unit Dose of Dentifrice

| Ingredients | % |
|---|---|
| Glycerine | 25.00 |
| Sorbitol | 22.75 |
| Coconut Oil | 10.00 |
| Na Alginate | 1.00 |
| Xanthan | 0.50 |
| Na Saccharin | 0.25 |
| Na Benzoate | 0.50 |
| TiO$_2$ | 0.50 |
| H$_2$O | 20.00 |
| Zeo 49 | 18.00 |
| Sodium Lauryl Sulfate | 0.80 |
| Spearmint Flavor | 0.70 |

This unit dose dentifrice prepared as in Example 1, is effective similar to that of Example 1.

EXAMPLE 4

Unit Dose Form

| Ingredients | Mouthrefreshener % |
|---|---|
| Glycerine 99.3% | 10.00 |
| Avocado Oil | 10.00 |
| Sodium Alginate | 1.00 |
| Sodium Saccharin | 0.25 |
| Flavor | 0.15 |
| Deionized Water | 78.60 |

A fluid alginate gel mixture of the above ingredients is extruded in droplet form into an aqueous bath containing 5% calcium chloride. About 15-20 beads are dropped into said solution. The droplets form beads and float to the surface of the bath. The beads are removed therefrom and rinsed in deionized water and dried in a forced air convection oven. The resulting beads are encapsulated flavor in the form of a jelly type mouth refreshener. These beads are preferably coated with a sodium carboxylmethyl cellulose, kappa carrageenan or other edible coating material.

Other dental polishing agents may be substituted for the siliceous polishing agent of Examples 1-3 such as hydrated alumina, calcined, alumina and the alkaline earth metal phosphates. Other crosslinking calcium compounds may be substituted for the calcium chloride in the setting bath, such as calcium sulfate or calcium lactate. Additives such as a fluoride; antiplaque and antitartar agents such as zinc compounds, quaternary ammonium compounds and the guanidines such as biguanide compounds; coloring agents or dyes may be incorporated into the unit dose formulations.

Although this invention has been described with reference to specific examples, it is understood that modifications and variations of compositions and procedure are contemplated within the scope of the following claims.

What is claimed:

1. A stable, chewable single unit dose, freestanding form of an oral product, stabilized against syneresis, comprising about 0.4-1.5% by weight of a sodium alginate crosslinked with a calcium ion, about 0.1-5.0% by weight of a flavor and at least 40% by weight of a liquid vehicle containing at least 10% by weight water, and at least 5% by weight humectant, and about 2-15% by weight of a liquid vegetable oil.

2. A single unit dose form according to claim 1, which is in the form of a chewable unit dose form of a dentifrice or of a mouthwash or of a mouth freshener.

3. A single unit dose form according to claim 1 wherein the vegetable oil is selected from the group consisting of coconut oil, palm oil, avacado oil, peanut oil and safflower oil.

4. A single unit dose form of dentifrice according to claim 2, wherein the liquid vehicle comprises water, glycerin and sorbitol in an amount of about 40-75% by weight.

5. A single unit dose form of dentifrice according to claim 4 wherein the water content is about 10-50% by weight and the combined glycerin and sorbitol content comprises about 20-50% by weight of the formulation.

6. A single unit dose form of mouthwash according to claim 2, wherein the liquid vehicle constitutes about 55-95% by weight liquid comprising about 50-80% by weight water and about 5-15% by weight of at least one of glycerin and sorbitol.

7. A single unit dose form of dentifrice according to claim 5, containing about 5-25% by weight of a dentally acceptable water insoluble polishing agent.

8. A single unit dose form of dentifrice according to claim 7, wherein the polishing agent is a siliceous polishing agent.

9. A single unit dose form of dentifrice according to claim 5 containing about 0.5-1.5% by weight of a substantially water soluble gum selected from the group consisting of iota carrageenan, xanthan, gum arabic, kappa carrageenan, sodium carboxymethyl cellulose, methyl cellulose, hydroxyethyl cellulose and hydroxypropyl cellulose.

10. A single unit dose form of dentifrice according to claim 9 wherein the ratio of sodium alginate:gum is about 1:1.6 to 2:1.

11. A single unit dose form of dentifrice according to claim 10, wherein the gum is iota carrageenan.

* * * * *